United States Patent [19]
Buhler et al.

[11] Patent Number: 5,592,943
[45] Date of Patent: Jan. 14, 1997

[54] APPARATUS AND METHOD FOR ACOUSTIC ANALYSIS OF BONE USING OPTIMIZED FUNCTIONS OF SPECTRAL AND TEMPORAL SIGNAL COMPONENTS

[75] Inventors: Joe P. Buhler, Portland; David Butt, Beaverton; Jeffrey H. Goll, Lake Oswego; Harold R. McCartor, Portland; Stuart H. Rowan, Banks; Neldon C. Wagner, Aloha; Hartwell H. Whitney, Portland, all of Oreg.

[73] Assignee: Osteo Sciences Corporation, Beaverton, Oreg.

[21] Appl. No.: 404,813

[22] Filed: Mar. 13, 1995

Related U.S. Application Data

[63] Continuation of Ser. No. 43,870, Apr. 7, 1993, Pat. No. 5,396,891.

[51] Int. Cl.⁶ ........................................................ A61B 8/00
[52] U.S. Cl. ........................................................ 128/661.03
[58] Field of Search ................... 128/660.01, 660.06, 128/661.03, 660.02; 73/597, 599

[56] References Cited

U.S. PATENT DOCUMENTS

| | | | |
|---|---|---|---|
| 5,038,787 | 8/1991 | Antich et al. | 128/660.08 |
| 5,228,445 | 7/1993 | Pak et al. | 128/660.01 |
| 5,309,898 | 5/1994 | Kaufman et al. | 601/2 |
| 5,343,863 | 9/1994 | Wiener et al. | 128/660.01 |
| 5,396,891 | 3/1995 | Whitney et al. | 128/661.03 |

*Primary Examiner*—Francis Jaworski
*Attorney, Agent, or Firm*—Bromberg & Sunstein

[57] ABSTRACT

An apparatus and method for acoustic analysis of bone are disclosed which provide measurements of transient spectral or temporal characteristics using signal processing techniques, wherein ultrasonic bone index value measurements are derived so as to minimize differences among successive measurements taken of the same individual and to maximize differences in measurements taken of different individuals and provide outputs indicating the condition of bone.

17 Claims, 12 Drawing Sheets

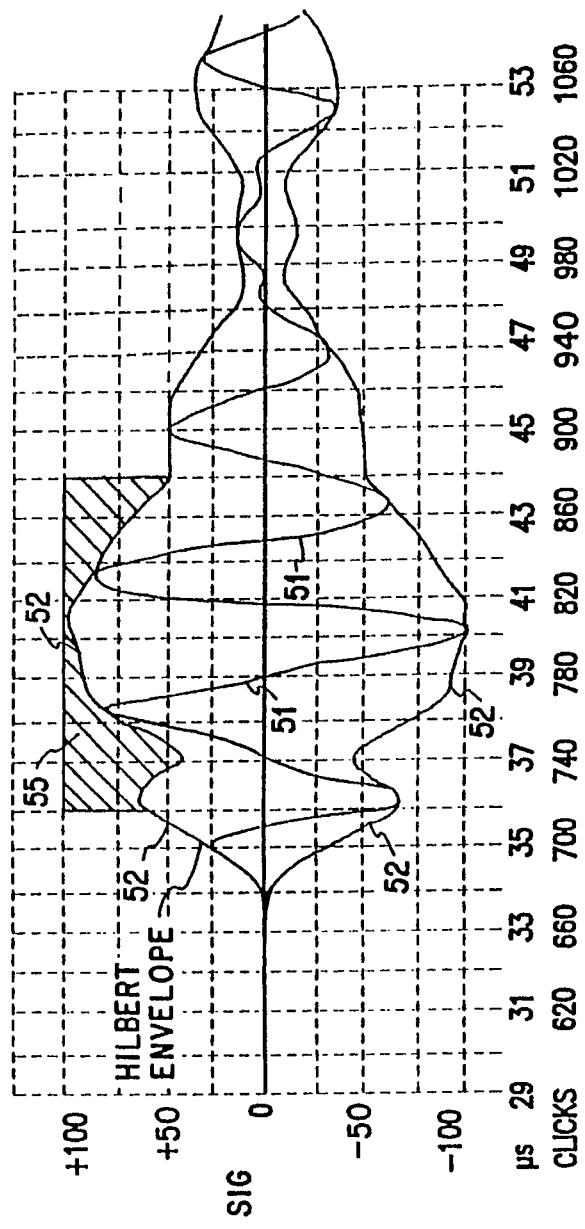
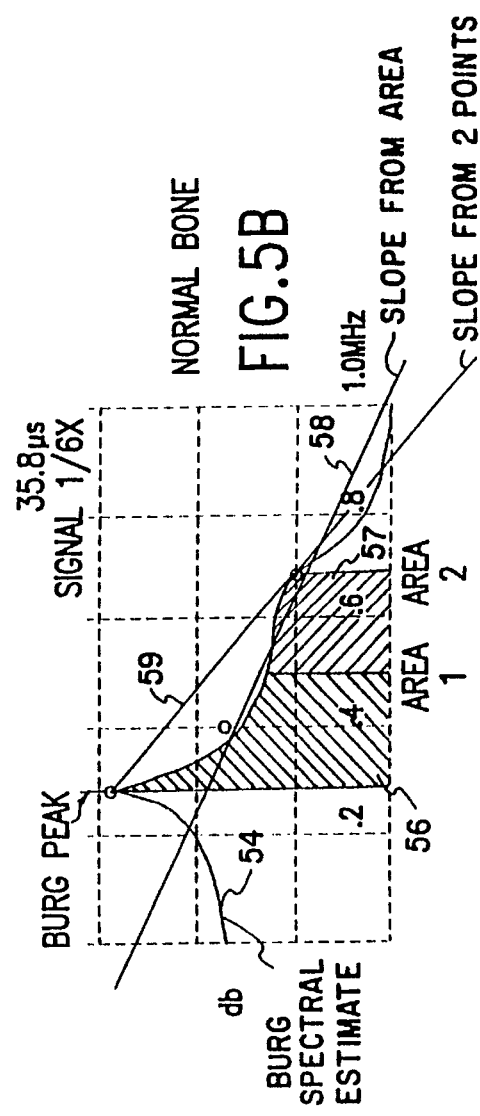

APPARATUS AND METHOD FOR ACOUSTIC ANALYSIS OF BONE USING OPTIMIZED FUNCTIONS OF SPECTRAL AND TEMPORAL SIGNAL COMPONENTS

The present application is a continuation of U.S. application Ser. No. 08/043,870, filed Apr. 7, 1993, issued on Mar. 14, 1995 as U.S. Pat. No. 5,396,891; this related application is hereby incorporated herein by reference.

TECHNICAL FIELD

The present invention relates to apparatus and methods for the acoustic analysis of bone, and more particularly to apparatus and methods for accomplishing bone measurement using signal processing techniques.

BACKGROUND ART

The prior art is rich with approaches to measurement of bone characteristics using acoustic and other methods with a view to identifying patients in need of treatment for osteoporosis. Many acoustic techniques utilize a first transducer to provide an acoustic signal, typically at ultrasonic frequencies, to the subject from a first external location and a second transducer at a second external location disposed on the opposite side of the bone of interest to receive the signal transmitted by the first transducer through the bone and intervening soft tissue. (The transducers are typically coupled to the subject through a suitable fluid, such as water.) Under one approach, there is determined the rate of Broadband Ultrasound Attenuation (BUA) in the range of approximately 300 to 700 kHz. The BUA is determined by measurement of the attenuation at a plurality of frequencies and then fitting the measurements to a suitable linear logarithmic-amplitude versus frequency scale. However, as an indicator of osteoporotic bone, BUA does not provide a desirable level of specificity and sensitivity.

A survey of prior art bone characteristic measurement is provided in the excerpt, from a document prepared by Merck & Co., Inc., which is submitted herewith and incorporated herein by reference as background material. (The discussion in this document of the Osteo Sciences Ultrasonometer is not prior art.)

The present invention provides, in some embodiments, enhanced specificity and sensitivity in detecting osteoporotic bone by utilizing a number of surprising discoveries, including: (i) the attenuation of ultrasound in bone is nonlinear, and utilization of received signal information that is lost in BUA analysis permits more accurate assessment of bone condition; and (ii) significant portions of the acoustic energy lost in attenuation in direct transmission through the bone can be measured by suitable placement of a third transducer in a position distinct from the path of direct transmission.

In accordance with a preferred embodiment of the invention, there is provided an apparatus for externally measuring in a vertebrate subject the extent of osteoporosis of a bone. The embodiment has first and second transducers and a mounting arrangement for mounting the transducers in spaced relationship with respect to the bone. A signal generator, in communication with the first transducer, causes the first transducer to produce acoustic signals, having energy distributed over a frequency range, that are propagated into the subject and received by the second transducer along a path that includes the bone. Finally, the embodiment has a signal processor, in communication with the second transducer, for providing a measurment that is a function of at least one of spectral or temporal components of the signal received by the second transducer. The function is selected for its ability to minimize differences among successive measurements taken of the same individual and to maximize differences in measurements taken of different individuals, so that the measurement relates to the extent of osteoporosis of the bone. In a further embodiment, the function is a weighted sum of spectral components of the signal received by the second transducer, and the weights are selected for their ability to minimize differences among successive measurements taken of the same individual and to maximize differences in measurements taken of different individuals.

BRIEF DESCRIPTION OF THE DRAWINGS

The foregoing features of the present invention will be more readily understood by reference to the following detailed description taken with the accompanying drawings, in which:

FIG. 5A provides a plot showing the stored output of transducer 13 FIG. 1 in response to an excitation waveform, generated by the system of FIG. 1 and transmitted from transducer 12 through a bone of low-normal quality, as well as plots pertinent to calculation of UBIs in accordance with a preferred embodiment of the invention;

FIG. 5B provides a plot of the Burg spectral estimation function associated with the plots of FIG. 5A;

DETAILED DESCRIPTION OF SPECIFIC EMBODIMENTS

Figure 1:
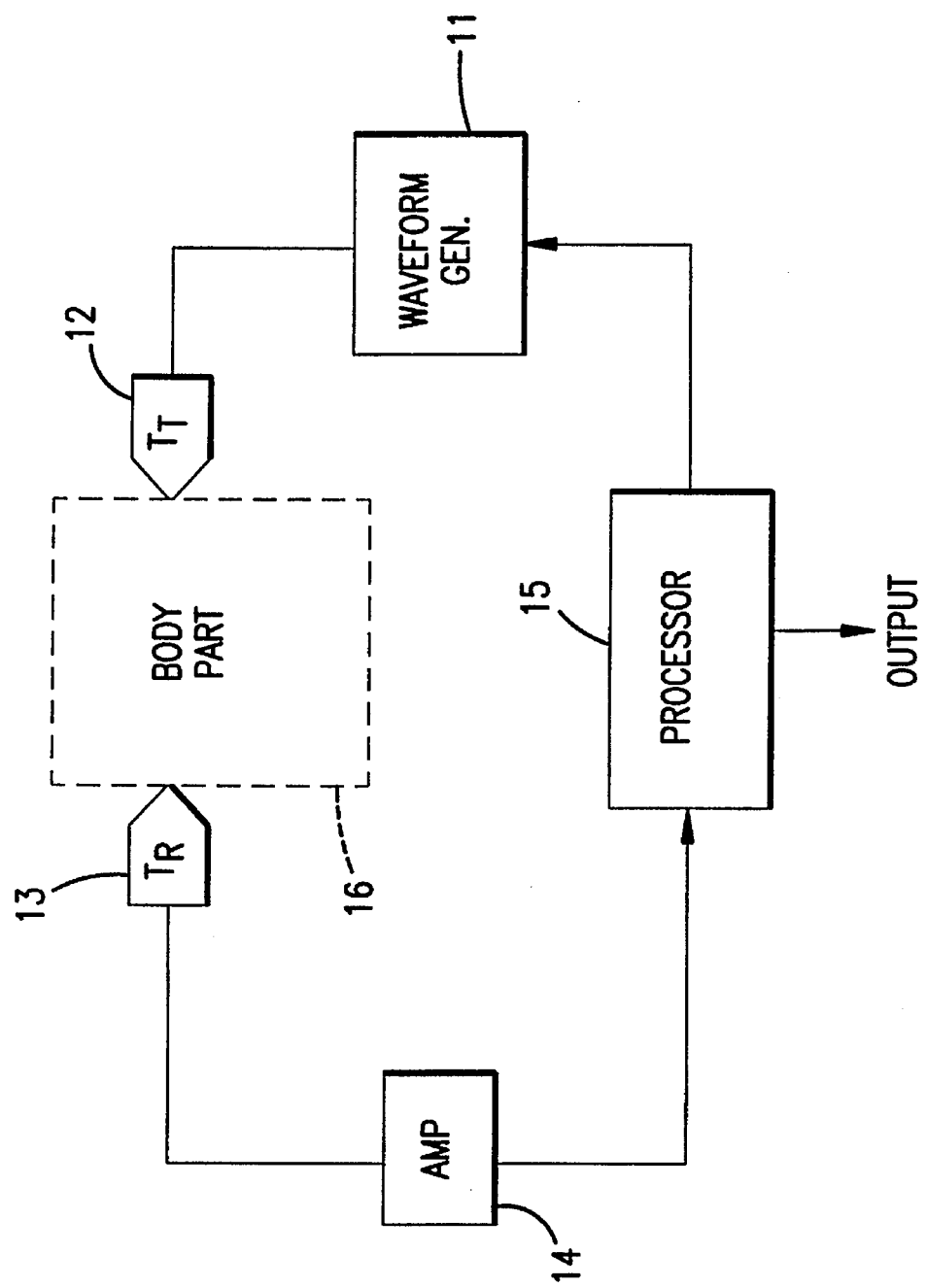
FIG. 1 is a diagram showing in general the components for a system in accordance with a preferred embodiment of the invention.

FIG. 1 is a diagram showing in general the components for a system in accordance with a preferred embodiment of the invention. In this system, a waveform is generated by waveform generator 11, and delivered to transmitting transducer $T_T$, item 12. The transducer $T_T$ is acoustically coupled to body part 16 of a subject and produces an acoustic wave that is propagated into the body part 16 and in particular into a bone within the body part. The transducer $T_R$, item 13, is also acoustically coupled to the body part 16 and receives a signal resulting from the effects, among other things, of propagation of the acoustic wave through the bone and the body part. The output of the transducer $T_R$ is amplified by amplifier 14 and processed by processor 15. The processor analyzes the output of the transducer $T_R$, and may make a determination reflective of the condition of the bone, and provides an output.

Figure 2:
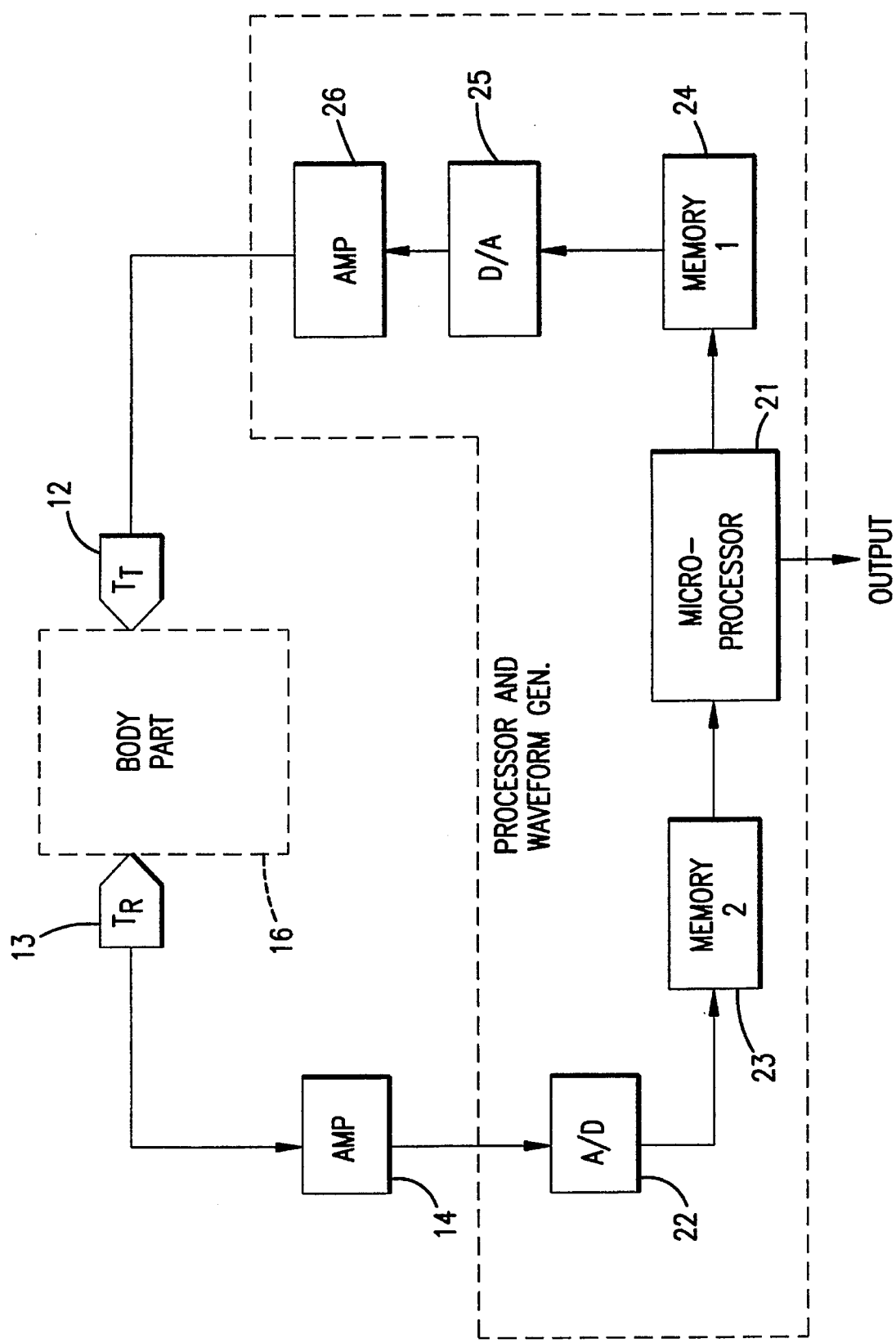
FIG. 2 is a diagram showing an implementation of the system of FIG. 1.

FIG. 2 is a diagram showing an implementation of the system of FIG. 1. While the elements of FIG. 1 may be implemented in analog components, in a manner known in the art, we have found it convenient to use a digital implementation. Accordingly, the processor 15 and waveform generator 11 are realized by a microprocessor 21 that controls both processing of the output from the transducer $T_R$ and the generation of the waveform used for transducer $T_T$. This waveform is stored in digitized form in memory 1, item 24, and trader control of the microprocessor is run through digital-to-analog converter 25 before being provided to amplifier 26 and the transducer $T_T$. Similarly, the output of receiving transducer $T_R$ is fed from amplifier 14 to analog-to-digital converter 22 and this digitized output is stored in memory 2, item 23. The stored output is then processed by the microprocessor 21, which provides a data output indicating the condition of the bone.

In further embodiments of the invention, the embodiments of FIG. 2 (or a wholly or partially analog implementation of FIG. 1) are used to process the stored output of $T_R$ in accordance with any one or more of a variety of procedures to provide a data output indicating the condition of the bone. In accordance with some embodiments, the data output indicating bone condition includes a number, which we call the "Ultrasonic Bone Index" (UBI). Each different procedure we employ can lead to a different UBI, and the various UBI types are identified by a numerical suffix, for example, UBI-2, UBI-3, etc. The procedures for UBI-2 through UBI-7 are described below. In connection with the general signal processing techniques utilized (but not there specific utilization in the context of ultrasonic bone testing), the following references are pertinent: Boualem Boashash, ed., *Time-Frequency Signal Analysis* (Wiley, 1992) (especially pertinent to instantaneous frequency analysis; see especially ch. 2, pages 43–73) and Richard Shiavi, *Introduction to Applied Statistical Signal Analysis* (Irwin, 1991) (especially pertinent to Burg Spectral Estimation; see especially pages 369–373). These texts are hereby incorporated herein by reference.

Our procedures have been developed to take advantage of the fact that healthy bone and osteoporotic bone respond differently to ultrasound inputs. Although it has been known, for example, that the rate of attenuation with frequency of ultrasound signals in bone may be indicative of bone condition, the prior art measure of such attenuation, namely broadband ultrasound attenuation (BUA), is based on the assumption that the attenuation is log-linear and provides a number associated with the rate of log-linear attenuation. Our investigations have led to the discovery that healthy and osteoporotic bone can be better distinguished by utilizing more information in the ultrasonic signals propagated through bone. We have found that the difference in effects, moreover, between healthy and osteoporotic bone is not one that can be measured wholly by looking the prior art BUA. The procedures outlined below take advantage of these and other observations.

Figure 3A:
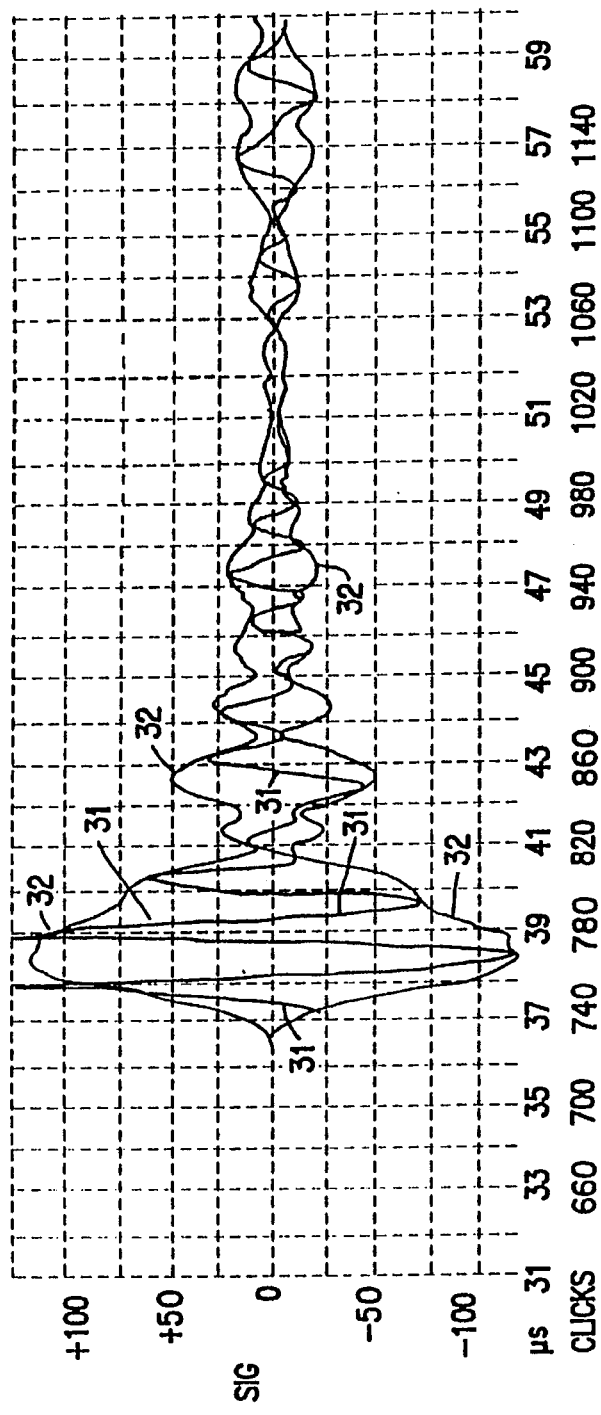
FIG. 3A provides a plot showing the stored output of transducer 13 of FIG. 1 in response to an excitation waveform, generated by the system of FIG. 1 and transmitted from transducer 12 through water only, as well as plots pertinent to calculation of UBIs in accordance with a preferred embodiment of the invention, shown here as controls.
Figure 3B:
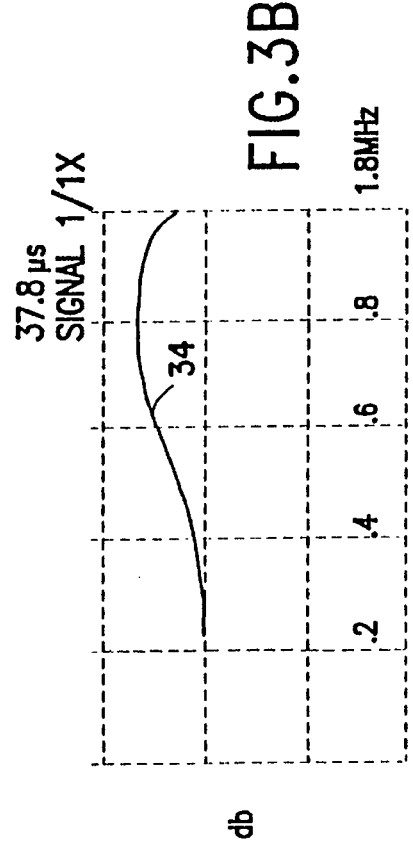
FIG. 3B provides a plot of the Burg spectral estimation function associated with the plots of FIG. 3A.
Figure 4A:
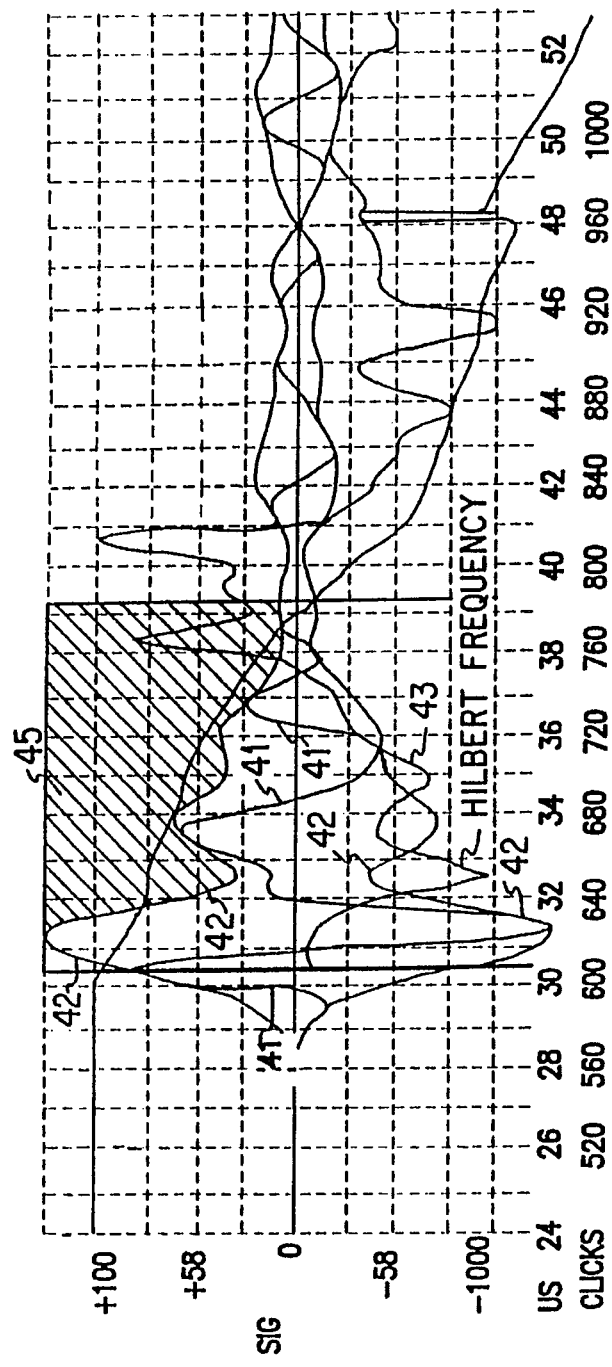
FIG. 4A provides a plot showing the stored output of transducer 13 FIG. 1 in response to an excitation waveform, generated by the system of FIG. 1 and transmitted from transducer 12 through an osteoporotic bone, as well as plots pertinent to calculation of UBIs in accordance with a preferred embodiment of the invention, FIG. 4B provides a plot of the Burg spectral estimation function associated with the plots of FIG. 4A.
Figure 4B:
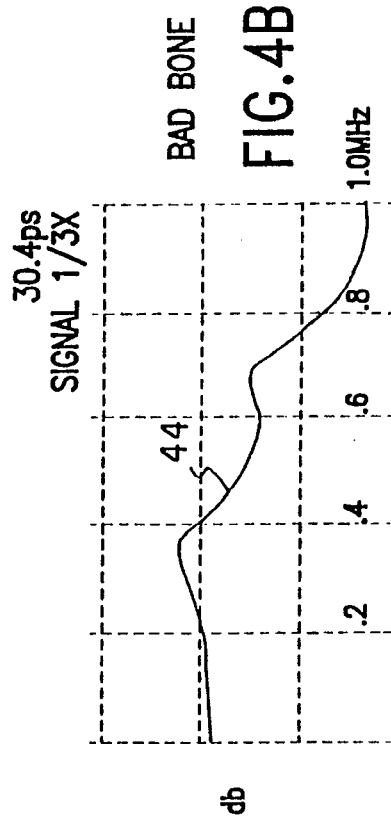
Figure 6A:
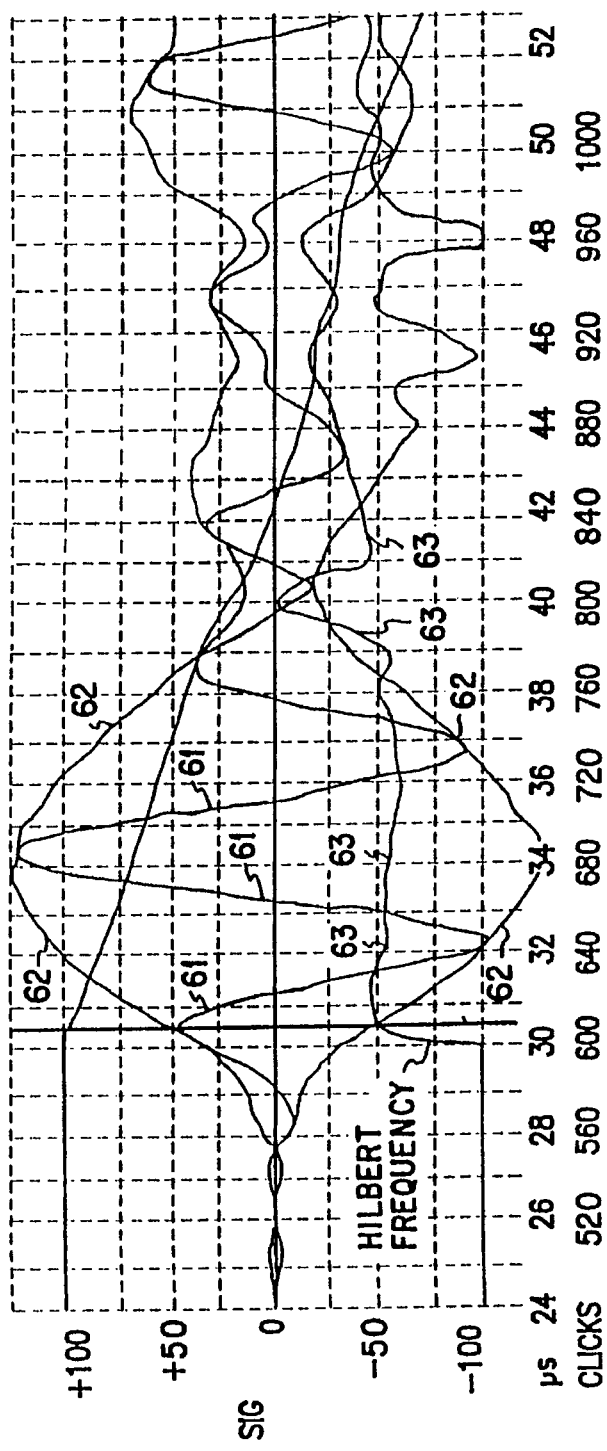
FIG. 6A provides a plot showing the stored output of transducer 13 FIG. 1 in response to an excitation waveform, generated by the system of FIG. 1 and transmitted from transducer 12 through an exceptionally healthy bone, as well as plots pertinent to calculation of UBIs in accordance with a preferred embodiment of the invention.
Figure 6B:
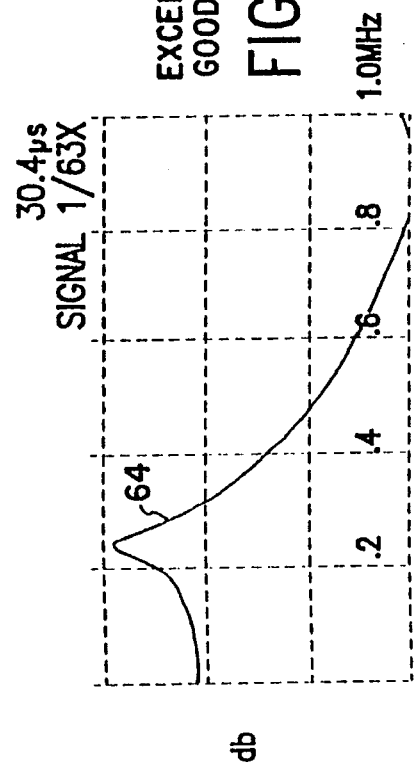
FIG. 6B provides a plot of the Burg spectral estimation function associated with the plots of FIG. 6A.

In the examples that follow, $T_T$ is supplied with a short pulse of about 500 nanoseconds duration. In this case the pulse has a sawtooth shape, with a rise time to the peak of about 300 nanoseconds and a decay time of about 200 nanoseconds. The sound output of $T_T$ is a short burst (with some ringing) having a fundamental frequency of about 1 MHz. Because $T_T$ is putting out a transient signal, however, useful components at frequencies within a range from about 200 kHz to 1 MHz are present as well. For the purposes of illustration of the nature of the burst, FIG. 3A provides a plot 31 showing the stored output of transducer 13 of FIG. 1 in response to an excitation waveform, generated by the system of FIG. 1 and transmitted from transducer 12 through water only. (FIG. 3A also shows the Hilbert envelope 32 of the waveform 31, while FIG. 3B shows the Burg spectral estimation function associated with the waveform 31. These concepts are discussed below.)

In accordance with UBI-2, the stored output of $T_R$ is run through a Fourier transform. A weighted linear sum of the logarithm of resulting frequency components is then computed; this sum is UBI-2. The weights are chosen to minimize differences among successive measurements taken of the same individual and to maximize differences in measurements taken of different individuals, so that the function acts as a discriminant in determining the presence or absence of osteoporotic bone. The weights may be selected empirically using manual techniques. They may also be selected using neural net techniques known in the art. See U.S. Pat. No. 5,259,384 for an invention of Kaufman. They also may be determined analytically in accordance with the method described below in the next two paragraphs.

An analytic method for optimization of linear coefficients method is described in this paragraph. Suppose that repeated observations are made on individuals in a population. Thus, in each experiment we measure a vector $v=(v_1, \ldots, v_n)$. (This vector v may, for example, constitute the magnitudes of n frequency components of the received signal; but it may be any other set of measurements associated with an individual, as discussed in further detail below.) We seek the coefficients $a_k$ of a linear combination of these vector components $v_k$, thus:

$$s = \sum_{k=1}^{n} a_k v_k,$$

in such a way that the "score" s minimizes the variance attributable to repeated measurements taken of the same individual while at the same time maximizing the range of the score and approximately conforming to our prior notions of how the individual should score. Thus $\alpha_k$ is a "weight" assigned to the k-th variable $v_k$ of the vector v, and we are searching for an optimal weighted linear combination of the variables. In order to specify the method for doing this, we assume that the repeated measurements have been made that lead to vectors v(i,j), which are the results of the j-th measurement on individual i. A weighting vector $a=(a_k)$ ($k=1, \ldots, n$) leads to a score of the form $$S_a(v(i,j)) = \sum_{k=1}^{n} a_k v(i,j)_k.$$

The mean score on individual i is $S_a(v(i))$, where $$v(i) = \frac{1}{N_i} \sum_{j=1}^{N_i} v(i,j)$$

is the mean of the observations on individual i and $N_i$ observations are made on individual i. The average "within-individual" variance, where there are N individuals, is therefore $$I(a) = \frac{1}{N} \sum_{i=1}^{N} \frac{1}{N_i - 1} \sum_{j=1}^{N_i} (S_a(v(i,j)) - S_a(v(i)))^2.$$

Now let $$v = \frac{1}{N} \sum_{i=1}^{N} v(i)$$

be the average of the observations of all individuals. Then the "between-individuals" population variance is $$P(a) = \frac{1}{N-1} \sum_{i=1}^{N} (S_a(v(i)) - S_a(v))^2$$

We want to find a scoring vector such that the quotient $$\frac{I(a)}{P(a)}$$

is minimized. This "generalized Rayleigh quotient" is a quotient of quadratic forms, and is optimized by choosing a minimal generalized eigenvalue λ where Aa=λBa and where the matrices A and B correspond to the quadratic forms in the usual way:
   $I(a)=a^{tr}$ A a, $P(a)=a^{tr}$ B a.

The calculation of these generalized eigenvalues can be performed in several ways well known in the art. See for example, J. Stoer and R. Bulirsch, *Introduction to Numerical Analysis* (Springer-Verlag, New York, Second Edition, 1991), page 405, which discusses generalized eigenvalue problems. The upshot is that the coefficients of an optimal linear model built on the data v can be obtained by combining the observed data into the above linear model.

It is possible to incorporate prior subjective scores into this procedure. More precisely, suppose that we believe that individual i should have the score $s_i$. Then we modify the above problem by replacing I(a) by $$I(a) + t \sum_{i=1}^{N} (a_{n+1} + a_{n+2}s_i - S_a(v(i)))^2$$

where t is a parameter that determines how heavily we want to force the computed scores to match our prior beliefs. The resulting problem is identical in form to the prior one, except that there are two new variables $\alpha_{n+1}$ and $\alpha_{n+2}$. If the parameter t is large then this becomes a linear regression problem. If the parameter is small, then we are more interested in minimizing the average variance (as a fraction of the population variance) as above. The method assumes that the scores should depend only linearly on the measured values. We find that experimentation is valuable, both for choosing which observations to consider, and for choosing the parameter t.

It will be appreciated that the weights determined using any of the procedures above are dependent on the precise characteristics of the system employed, including characteristics of the transducers, the waveform input to $T_T$, the circuits and processing associated with the signal from $T_R$, and the data with respect to which the weights are optimized. A sample set of weights for UBI-2 is set forth in Table 1 below.

TABLE 1

| Frequency (MHz) | Program Weights | Simplified Weights | Constrained Weights |
|---|---|---|---|
| 0.000 | 0.0718 | 0.0 | 0.0 |
| 0.125 | 1.0000 | 1.0 | 1.0 |
| 0.250 | 0.225 | 0.2 | 0.0 |
| 0.375 | −0.406 | −0.4 | −0.4 |
| 0.500 | −0.0767 | 0.0 | 0.0 |
| 0.625 | −0.506 | −0.5 | −0.6 |
| 0.750 | −0.0372 | 0.0 | 0.0 |
| 0.875 | −0.139 | −0.1 | 0.0 |
| 1.000 | −0.0365 | 0.0 | 0.0 |
| 1.125 | −0.0486 | 0.0 | 0.0 |
| 1.250 | 0.0946 | 0.0 | 0.0 |
| 1.375 | −0.00858 | 0.0 | 0.0 |

The data in Table 1 was derived from data collected on 21 subjects. The weights for each frequency component used in UBI-2 appear in columns 2, 3, and 4. In the second column are weights as calculated using the analytical approach discussed above. In the third column are the weights resulting after using only the five largest weights and then rounding to one significant figure. This column produces results that are only slightly degraded from those using the weights in column 2. In column 4 are weights resulting after using only the three largest weights and then modifying them slightly so that they sum to 0. The column produces results that in turn are only slightly degraded from those using the weights in column 3. It is preferred to use weights in this context that sum to 0, so that a change in gain does not produce a change in the resulting UBI-2. Note that the weights in Table 1 are greatest in the regions of 100–200 kHz (positive) and 500–700 kHz (negative).

The UBI-3 procedure utilizes the Hilbert envelope of the stored output of $T_R$; the Hilbert envelope provides a measure of the energy content of the received waveform as a function of time. The greater preponderance of low frequency signals in the received waveform associated with healthy bone causes it to have a longer duration than in the received waveform associated with osteoporotic bone. Accordingly, in accordance with UBI-3, the Hilbert envelope is examined for energy duration. A relevant time period of the stored output is examined; for this time period, there is determined the area lying above the plot (of the top half of the envelope) and beneath a fixed value defined by the first peak in the plot. In one embodiment, the relevant period begins 1 microsecond after the first peak in the Hilbert envelope and continues for a total of 8 microseconds. In a further embodiment, UBI-3 is instead the curvature of the envelope over the first few microseconds following the first peak.

FIGS. 3A, 4A, 5A, and 6A are illustrative for the case of transmission through water, osteoporotic bone, low-normal bone, and exceptionally healthy bone respectively. Plots 31, 41, 51, and 61 show the stored output of transducer $T_R$ for such respective circumstances, and plots 32, 42, 52, and 62 show the corresponding Hilbert envelopes. It can be seen that hatched region 45, corresponding to the UBI-3 for an osteoporotic bone, is much larger than hatched region 55, corresponding to the UBI-3 for a low-normal bone.

The UBI-4 procedure utilizes the Burg spectral estimation function of the stored output of $T_R$; the Burg function provides a plot estimating power versus frequency of the received waveform. The shape of the plot is a discriminant between healthy and osteoporotic bone. UBI-4 is an estimate of the slope; generally the more steeply negative the slope, the healthier the bone. In this connection, see plots 34, 44, 54, and 64 in FIGS. 3B, 4B, 5B, and 6B respectively for the case of transmission respectively through water, osteoporotic bone, low-normal bone, and exceptionally healthy bone. In one embodiment, the UBI-4 slope of the plot is determined by best fit to the plot using mean square error. In another embodiment, the slope is determined in reference to the areas of two adjacent frequency regions, each of 200 kHz in width; the first frequency region starts at the first peak in the plot and the second frequency region starts 200 kHz higher. As an example, see areas 56 and 57 respectively in FIG. 5B, corresponding to the first and second regions. The proportional difference in these areas is indicative of the slope, which is shown as line 58 in FIG. 5B. In a further embodiment, the slope is determined by reference solely to two points on the plot, the first occurring at the first peak, and the second occurring 400 kHz higher in frequency. As an example, see line 59 in FIG. 5B.

The UBI-5 procedure utilizes the Hilbert frequency function. This function is plotted as item 43 and 63 in FIGS. 4A and 6A respectively for osteoporotic bone and exceptionally healthy bone respectively. It can be seen that for healthy bone, during the early portion (3 or 4 microseconds) of the received waveform, there is little variability, whereas for osteoporotic bone, there is considerable variability including higher frequencies than for healthy bone. The variability can be quantified according to any of a variety of methods well-known in the art.

The UBI-6 procedure utilizes the short-time Fourier transform of the stored output of $T_R$ to examine in more detail than with the Hilbert transform the varying spectral content of the received waveform over time. A frequency index may be computed in a fashion analogous UBI-2 or UBI-4. The temporal variation of this index may be used to compute a different index in a fashion analogous to UBI-5.

The UBI-7 procedure utilizes the Fourier transform of the stored output of $T_R$ to produce data permitting a plot of phase versus frequency; the slope of this plot is a measure of velocity (as a function of frequency). The variation of velocity with frequency (i.e., group delay) is dispersion, which can be quantified according to any of a variety of methods. In the relatively porous bone that characterizes osteoporosis, there is relatively little dispersion; in the relatively dense bone that results in healthy subjects, there is relatively more dispersion.

Although any one of the UBIs discussed may be used alone, it is also possible to use combinations of any number of them to enhance sensitivity and specificity in identifying osteoporotic bone. Indeed a single composite UBI may be derived as a function (which need not be linear) of the UBIs described above. The function may be the weighted sum, and the weights may be determined in the manner described above in connection with UBI-2: empirically, or using neural networks, or using the closed form analytical procedure described above.

Figure 7:
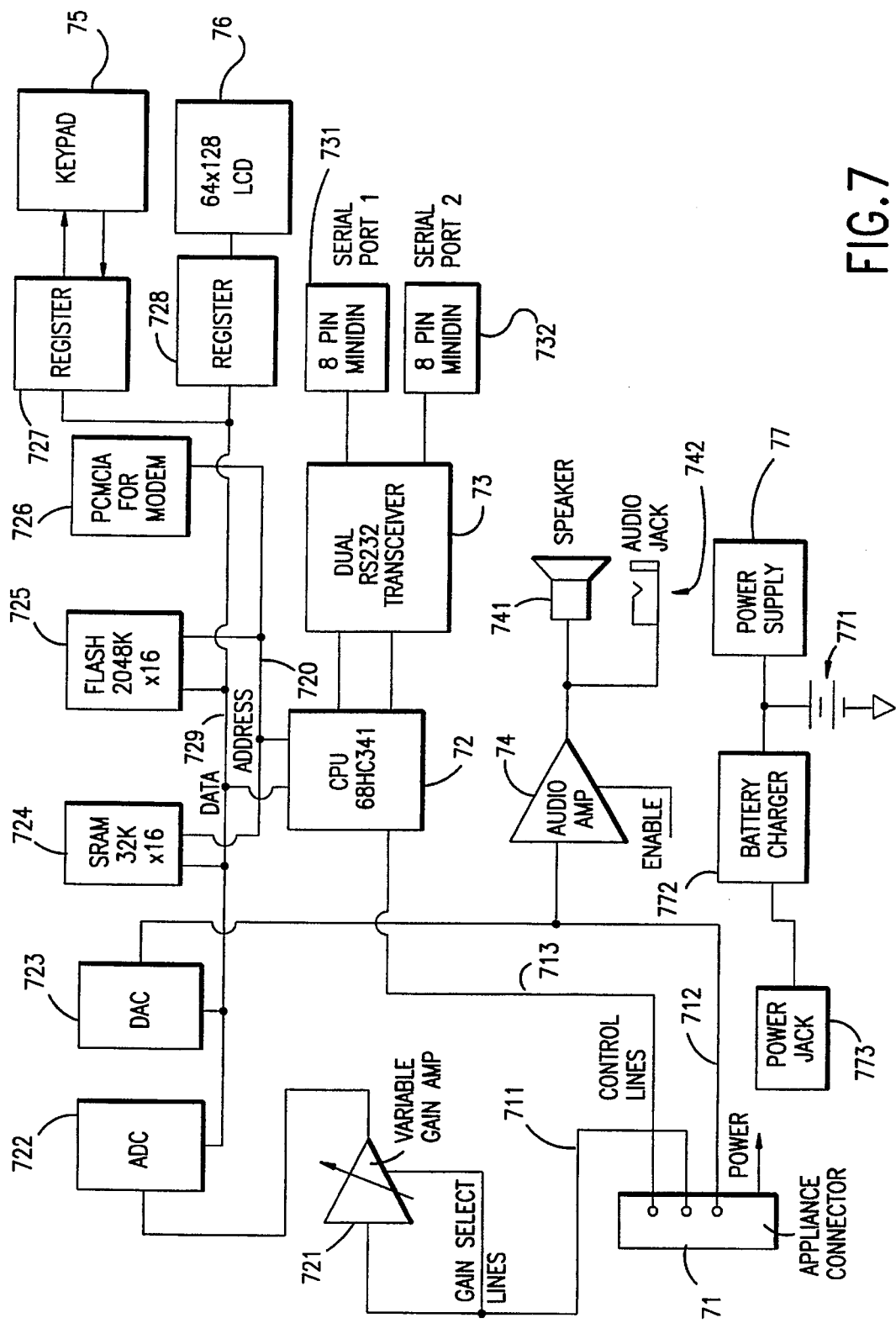
FIG. 7 is a diagram of a preferred embodiment of the implementation shown in FIG. 2.

The procedures described above may be employed in a device such as shown in FIG. 7, which is a diagram of a preferred embodiment of the implementation shown in FIG. 2. The device operates under the control of microprocessor 72, which is here implemented as a Motorola 68HC341. The microprocessor communicates with a data bus 729 and an address bus 720. In communication with these buses are static RAM 724 (here implemented as 32K times 16, to accommodate a 16-bit word), flash RAM 725 (here implemented as 2048K times 16), and PCMCIA slot 726 for communication via modem and potentially for other purposes. The device is also provided with first and second serial ports 731 and 732 respectively, coupled to the microprocessor 72 via dual RS-232 transceiver 73, for data input and output, permitting attachment of an external modem and direct communication with a PC. User input to the device is achieved locally via keypad 75, coupled to register 727, which is on the data bus 729. The device has a video output on display 76, here an LCD bit-mapped display having a resolution of 64×128 pixels, that is in communication with register 728 and data bus 720. The excitation waveform to drive the transducer $T_T$ of FIG. 2 is stored in Flash RAM 725 and is loaded into static RAM 724 over data bus 729; the static RAM transfers the waveform by direct memory access (DMA) into digital-to-analog converter 723, which provides an output over line 912 to appliance connector 71 to drive the transducer $T_T$. The waveform output from transducer $T_R$ of FIG. 2 is communicated to line 711 of connector 71, and then through variable gain amplifier 721 to analog-to-digital converter 722. The output of the converter 722 is communicated over data bus 729 to static RAM 724, where the received waveform data is captured. The data can then be processed by microprocessor 72 (according to the procedures described above), and UBI and other data can be presented to the user, both via the display 76 and over the ports 731, 732, and the PCMCIA slot 726. The transducers are here driven by a separate appliance module, described below in connection with FIG. 8, to which connection is made through appliance connector 71. The module is controlled by a dedicated microprocessor communication with which is over control line 713. Power is provided by power supply 77, which is coupled to battery 771 and battery charger 792, which in turn is connected to power jack 773.

In addition, we have found it valuable to provide a speaker 741 (audio jack 742 is also provided) coupled via audio amplifier 74 to digital-to-analog converter 723 to permit "listening" to the stored waveform received from transducer $T_R$. The listening is made possible by playing back the stored signal at 1/1000th of the original frequency and over an extended duration. The trained ear can distinguish many features of the waveform in this manner. The speaker can be used, moreover, similarly to listen to the waveform processed in other respects as well—processed, for example, in accordance with one or more of the UBI procedures described above. It can also be used to provide audible cues to the user, for example in positioning the appliance, so that a continuous analog signal indicative of position can guide the user, who will not then need to watch the display 76 while positioning the appliance.

Figure 8:
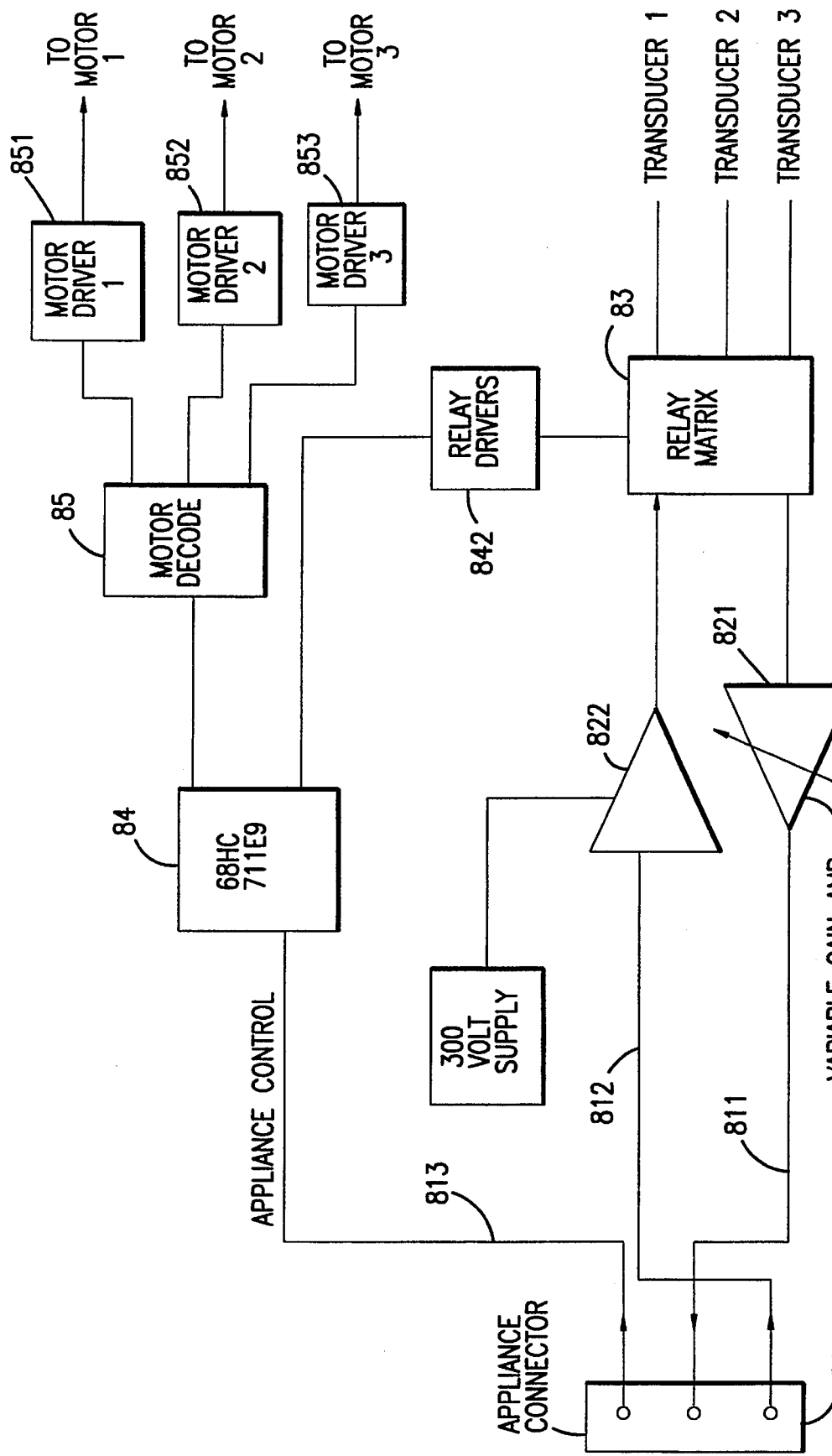
FIG. 8 is a diagram of the appliance circuit module used in connection with the embodiment of FIG. 7.

FIG. 8 is a diagram of the appliance circuit module used in connection with the embodiment of FIG. 7. The appliance connector 81 of FIG. 8 mates with connector 71 of FIG. 7. Control line 713 of FIG. 7 is connected through the connectors to control line 813 of FIG. 8, so that control signals run between slave microprocessor 84 (implemented here as Motorola 68HC711E9) and main microprocessor 72 of FIG. 7. The excitation line 712 of FIG. 7 is connected through the connectors to line 812 of FIG. 8 and driver amplifier 822, which is powered by a 300 volt supply. The received waveform line 711 of FIG. 7 is connected through the connectors to line 811 of FIG. 8 which receives an output from variable gain amplifier 821. The output of amplifier 822 and the input of amplifier 821 are connected to a relay matrix 83 that is driven by relay drivers 842 under control of microprocessor 84.

The relay matrix 83 permits the input of amplifier 821 to be connected to any of a series of, say, three transducers and the output of amplifier 822 to be connected to any other of the series of transducers. This arrangement has the advantage that the specific transducers used for transducers $T_T$ and $T_R$ may be switched, as desired, to assure symmetry of the system in either configuration and/or to compensate for the lack of symmetry. It also permits the use of a third transducer for a variety of purposes, including those described in the parent application, wherein three transducers are used in velocity measurements.

We have also found that when two transducers are used for the UBI procedures described above (involving ultrasound transmission in a direction transverse to the long axis of the tibia through the calcaneus), and using transducers of the type described below in connection with FIG. 11 (which behave predominantly like point sources), a substantial portion of the waveform energy not transmitted directly through the calcaneus can be detected by positioning a third transducer in a position distinct from the second transducer around the periphery of the heel to receive scattered or backscattered acoustic radiation. The signal from this third transducer can provide information complementary to that obtained with the initial two transducers associated with direct transmission.

The microprocessor 84 also communicates optionally with motor decoder 85, which is coupled to drivers 851, 852, and 853 for motors 1, 2, and 3 respectively. These motors control the position of the transducers relative to the body part including the bone trader measurement. The motors may be usefully used to assure correct positioning of the transducers for the measurements being made. Indeed, it appears that osteoporosis may appear preferentially not only in certain bones of a subject but also in one or more regions of such certain bone, such as the calcaneus. In accordance with an embodiment of the present invention, one or more of the transducers $T_T$ and $T_R$—and (in a further embodiment) both such transducers—are moved, over a pertinent region of the bone, either by the user or under microprocessor control, until an optimized reading (determined by one or more of the above procedures or otherwise) has been obtained, and then the measurements in the position associated with this optimized reading in accordance with the above procedures are completed and stored.

Figure 9:
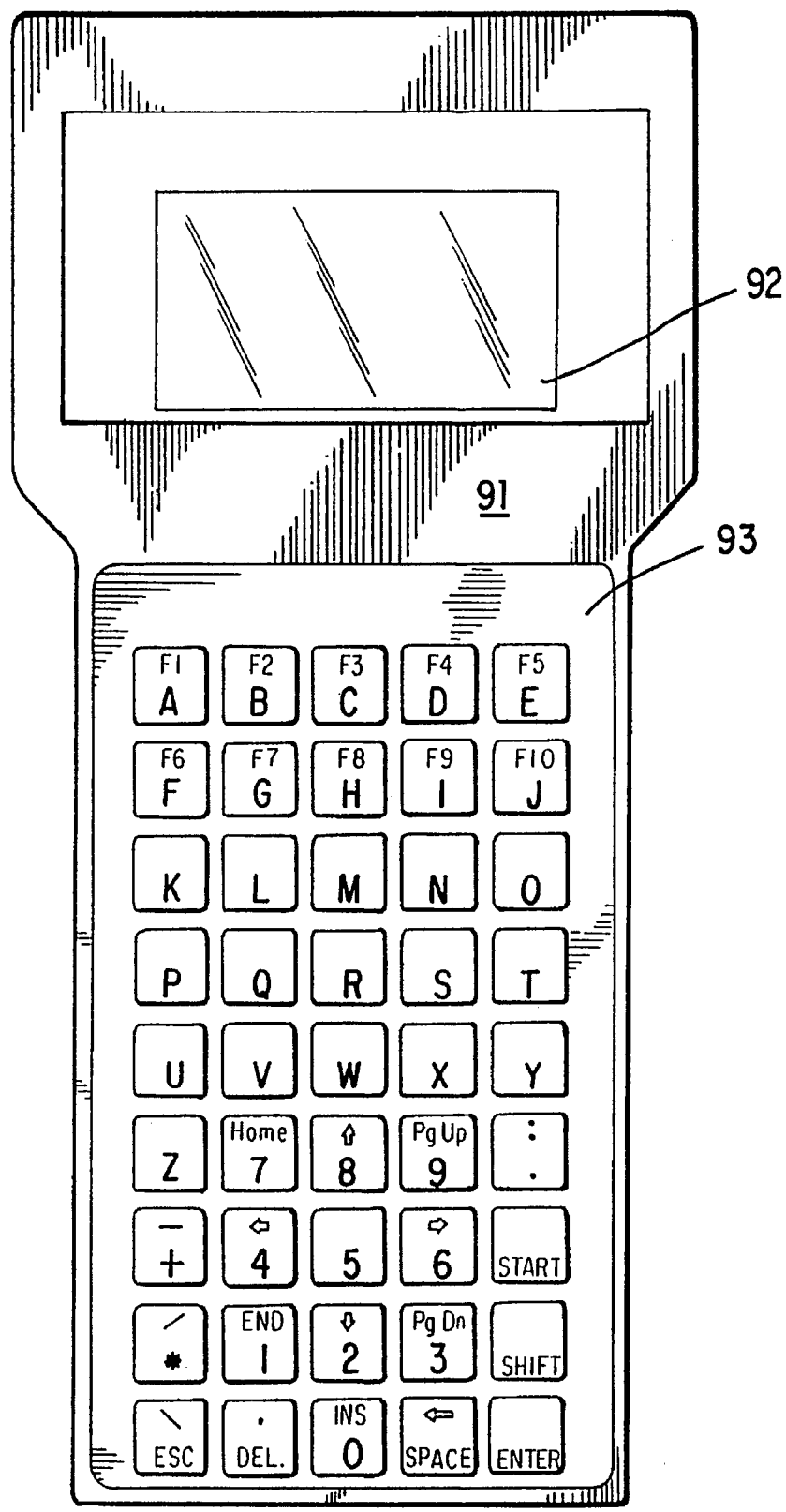
FIG. 9 is a front view of a hand-held device according to the embodiment of FIG. 7.

FIG. 9 is a front view of a hand-held device according to the embodiment of FIG. 7. All of the circuitry of the device of FIG. 7 is contained in a single unit, permitting excitation of the appliance transmitting transducer and processing of waveform data from the appliance receiving transducer(s) and storage and display of the results. The device has a housing 91, in which is provided the display 92 (item 76 of FIG. 7) and keypad 93 (item 75 of FIG. 7). The device also has the ports and other features described above in connection with FIG. 7.

Figure 10:
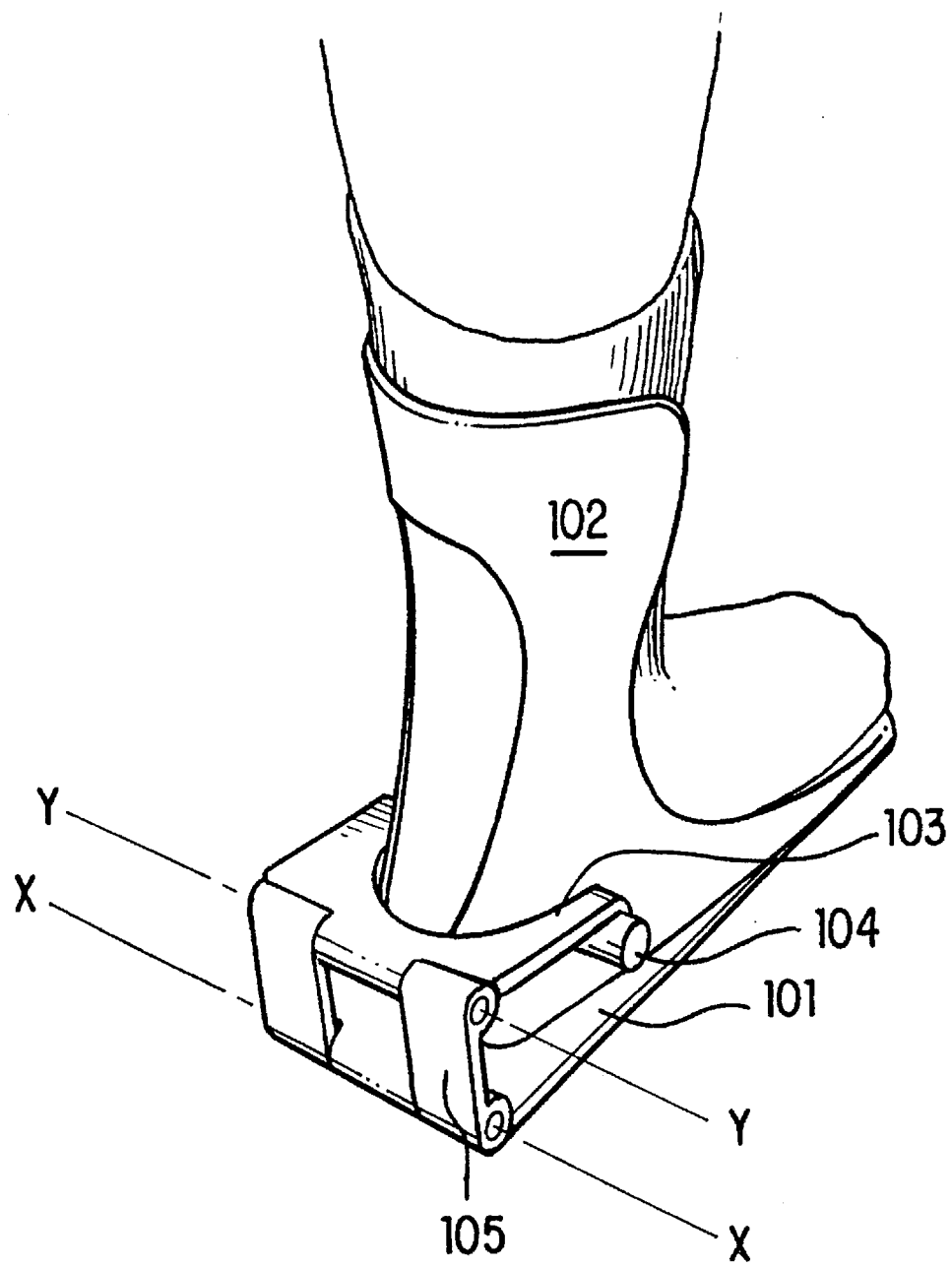
FIG. 10 is a rear view of an appliance in accordance with an embodiment of the invention.

FIG. 10 is a rear view of an appliance in accordance with an embodiment of the invention. The appliance includes a base 101 to which is attached rigidly a cradle 102 for the subject's foot and ankle. The subject's heel (and, if desired, neighboring regions) may be bare, or it may be placed, for purposes of hygiene, in a glove-like covering. To assure good ultrasound conduction, the covering is preferably thin, tight-fitting, and elastic. Alternatively, or in addition, the covering may be coated on the inside with a suitable material, such as a water-based gel, to assist in ultrasound conduction. (The effects of these materials may be compensated in signal processing of the received waveform.) The region of the cradle 102 corresponding to the calcaneus includes a cutout on each side to accommodate a receiving transducer on one side and a transmitting transducer on the other side. The transducers are mounted in generally opposed relation to one another (in location 104 for the lateral transducer [marked by a pen in the informal drawing]) in a yoke 103 that is movably mounted relative to the base 101 and cradle 102. In this embodiment the yoke 103 has two degrees of freedom, achieved by mounting the yoke 103 via a hinge at axis Y—Y to backplate 105, and mounting the backplate 105 via a hinge at axis X—X to the base 101. (The appliance module of FIG. 8 may suitably be physically mounted on the backplate 105.)

The position of the transducers may be monitored by using potentiometers, shaft encoders, or other suitable sensors disposed in relation to the axes X—X and Y—Y. In addition, the sensors are preferably biased inwardly toward each other (by one or more springs or other means) to assure good contact with the heel area of the subject for ultrasound transmission. If desired, the distance between the transducers can be determined indirectly, by mounting each transducer on a separate arm that is pivotally mounted at one end to the yoke, and the angle that the arm makes at the pivot can be monitored by suitable sensors; the arm angles, in combination with a knowledge of the geometry of the yoke assembly, can be used to calculated the distance between the transducers. Such distance information is useful for ultrasound velocity determinations.

Figure 11:
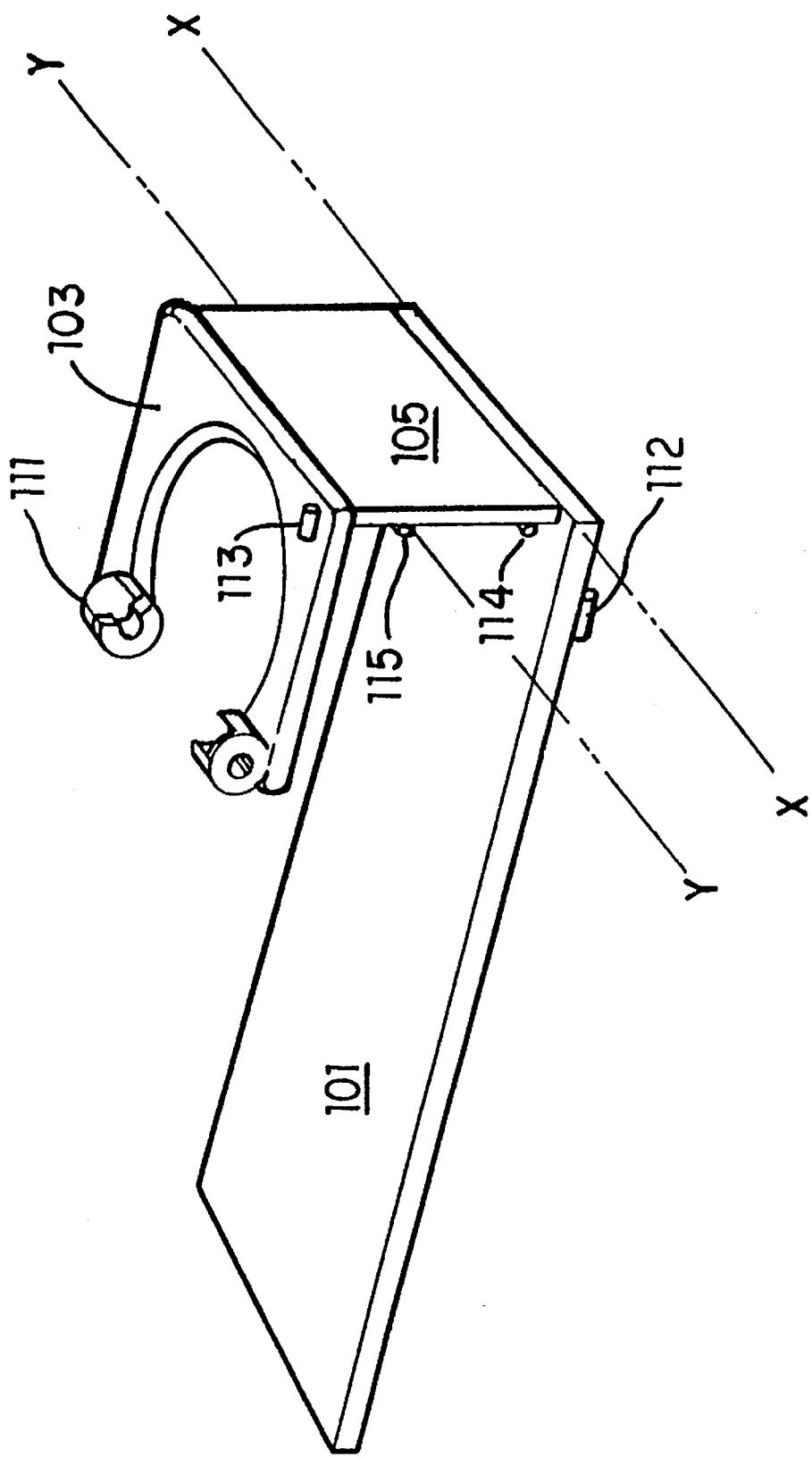
FIG. 11 shows an embodiment of the appliance of FIG. 10, equipped with magnets and hall effect devices to monitor the location of the transducers.

FIG. 11 shows an embodiment of the appliance of FIG. 10, equipped with magnets and hall effect devices to monitor the location of the transducers, mounted in the yoke 103, in holders 111. In this embodiment a first ceramic magnet 112 is mounted on the base 101 and a second ceramic magnet 113 is mounted on the yoke 103. Hall effect magnetic sensors 114 and 115 are mounted on stalks on backplate 105 in to detect the magnetic fields of magnets 112 and 113 respectively. The signal strengths of the outputs from Hall effect sensors 114 and 115 are therefore indicative of the degree of rotation respectively of backplate 105 about axis X—X and of yoke 103 about axis Y—Y. These outputs are linearized with angle by geometrically aligning each magnet and sensor pair so as to combine the 1/r effect (at these distances) of magnet-sensor distance and the sine θ effect of sensor angle in the magnetic field. Accordingly, 0 the outputs of Hall effect sensors can be mapped, under microprocessor control, into suitable rectangular coordinates to identify the location of the transducers in relation to the subject's heel.

As discussed above in connection with FIG. 8, the yoke may be moved manually or it may be moved trader motor control by suitably mounted motors associated with each degree of freedom.

Figure 12:
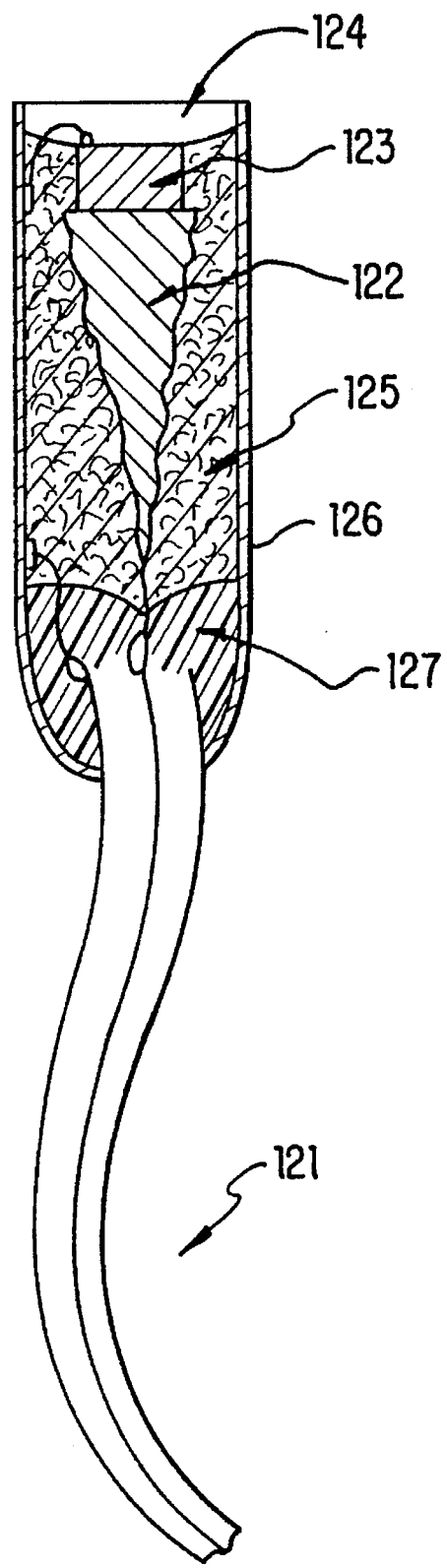
FIG. 12 is a cross-section of a transducer suitable for use in the appliance of FIGS. 10 and 11.

FIG. 12 is a cross-section of a transducer suitable for use in the appliance of FIG. 10. The transducer utilizes a piezo crystal element 123, which is unusual in that its aspect ratio is of the order 1.5:1. Such a ratio is usually viewed as undesirable, and more typical aspect ratios are at least 5 or 10:1, so as to avoid undesirable resonances in directions other than the transverse plane from which the ultrasound is to be propagated. In the present case, however, we have found that our design produces desirable resonances in that the transducer acts more like a point source. Typical dimensions for a piezo element of our design are a diameter of 0.125 inches (0.32 cm) and a thickness of 0.080 inches (0.20 cm). The element rests between metal base 122 and front face element 124, which are connected to the center and outside conductors respectively of a suitable coaxial cable 121. The transducer is disposed in a housing 126. The base 122 is placed within acoustically absorbent backing 125 to damp ringing, and the back end of the assembly is held in place with epoxy 127.

What is claimed is:

1. An apparatus for externally measuring in a vertebrate subject the extent of osteoporosis of a bone disposed within a body part, the apparatus comprising:
   (a) first and second transducers;
   (b) a mounting arrangement for mounting the transducers in spaced relationship with respect to the bone;
   (c) a signal generator, in communication with the first transducer, for causing the first transducer to produce acoustic pulses, having energy distributed over a frequency range, that are propagated into the subject and received by the second transducer along a first path that includes the bone;
   (d) a signal processor, in communication with the second transducer, for providing a measure that is indicative of at least one of transient spectral and transient temporal characteristics of a portion, up to the whole amount thereof, of a signal received by the second transducer, the measure being selected for its ability to minimize differences among successive measurements taken of the same individual and to maximize differences in measurements taken of different individuals, so that the measurement relates to the extent of osteoporosis of the bone.

2. An apparatus according to claim 1, wherein the function is a weighted sum, and the weights are selected for their ability to minimize differences among successive measurements taken of the same individual and to maximize differences in measurements taken of different individuals.

3. An apparatus for externally measuring in a vertebrate subject the extent of osteoporosis of a bone disposed within a body part, the apparatus comprising:
   (a) first and second transducers;
   (b) a mounting arrangement for mounting the transducers in spaced relationship with respect to the bone;
   (c) a signal generator, in communication with the first transducer, for causing the first transducer to produce acoustic pulses, having energy distributed over a frequency range, that are propagated into the subject and received by the second transducer along a first path that includes the bone;
   (d) a signal processor, in communication with the second transducer, for providing a single measure that is indicative of at least one of transient spectral and transient temporal characteristics of a portion, up to the whole amount thereof, of a signal received by the second transducer.

4. An apparatus according to claim 3, wherein the function includes a measure of the shape of the Hilbert envelope of a portion of the signal received by the second transducer.

5. An apparatus according to claim 3, wherein the function includes a measure of the shape of the Burg function of a portion of the signal received by the second transducer.

6. An apparatus according to claim 3, wherein the function includes a measure of the variability of the Hilbert frequency function of a portion of the signal received by the second transducer.

7. An apparatus according to claim 3, wherein the function includes a weighted sum of spectral components, determined using a short-time Fourier transform, and determined at successive intervals, of the signal received by the second transducer, wherein the successive weighted sums associated with successive intervals are themselves formed into a weighted sum.

8. An apparatus according to claim 3, wherein the function includes a measure of the group delay of a portion of the signal received by the second transducer.

9. An apparatus according to claim 3, further comprising:
   a third transducer, affixed to the mounting arrangement, for receiving, along a second path that is distinct from the first path, acoustic energy supplied by the first transducer.

10. An apparatus according to claim 3, wherein the second path is transverse to the first path.

11. An apparatus according to claim 3, wherein at least the first transducer includes a piezo crystal element that has an aspect ratio of diameter to thickness that is substantially less than 5:1.

12. An apparatus according to claim 11, wherein the aspect ratio is approximately 1.5:1.

13. A system for externally measuring in a vertebrate subject characteristic behavior of an acoustic wave in a bone disposed within a body part, the system comprising:
   (a) first and second transducers;
   (b) mounting means for mounting the transducers in spaced relationship with respect to the bone;
   (c) signal excitation means for causing the first transducer to produce an acoustic waveform that is propagated into the subject and received by the second transducer along a path that includes the bone;
   (d) characteristic determination means for determining a characteristic of the behavior of the waveform along the path;
   (e) a display for displaying outputs of the characteristic determination means; and
   (f) an appliance for removable engagement with the foot of a subject, the appliance having:
      (i) a base having a surface for receiving the sole of a foot having a longitudinal axis;
      (ii) a cradle rigidly attached to the base, for receiving the subject's foot and ankle, and disposed in a direction transverse to the base;
      (iii) a yoke for supporting the transducers in spaced relationship with respect to the bone;
      (iv) a member for mounting the yoke in moveable relationship to the base so as to permit joint two-dimensional motion of the transducers over regions of the heel including the calcaneous;
   wherein the yoke and member constitute the mounting means.

14. A system according to claim 13, wherein:
   the member is a backplate hingedly attached at one end to the base along a first hinge axis generally transverse to the longitudinal axis; and
   the other end of the backplate is hingedly attached, along a second hinge axis generally parallel to the first hinge axis, to the yoke.

15. An appliance for removable engagement with the foot of a subject, the appliance having:
   (a) a base having a surface for receiving the sole of a foot having a longitudinal axis;

(b) a cradle rigidly attached to the base, for receiving the subject's foot and ankle, and disposed in a direction transverse to the base;

(c) a yoke for supporting a pair of transducers in spaced relationship with respect to the heel of the foot;

(d) a member for mounting the yoke in moveable relationship to the base so as to permit joint two-dimensional motion of the transducers over regions of the heel including the calcaneous.

16. An appliance according to claim 13, wherein:

the member is a backplate hingedly attached at one end to the base along a first hinge axis generally transverse to the longitudinal axis; and the other end of the backplate is hingedly attached, along a second hinge axis generally parallel to the first hinge axis, to the yoke.

17. An appliance according to claim 13, further comprising:

a control module, physically mounted to at least one of the base, cradel, yoke or member, the module having a first set of data ports coupled to the transducers, a second set of data ports for coupling to (i) a signal excitation means for causing a first one of the transducers to produce an acoustic waveform that is propagated into the subject and received by a second one of the transducers along a path that includes the bone and (ii) characteristic determination means for determining a characteristic of the behavior of the waveform along the path; the control module including a microprocessor for controlling motors for causing displacment of the yoke and therefore the transducers over the calcaneous, the module having a control port over which the microprocessor receives control signals for the motors from a master microprocessor.

* * * * *

UNITED STATES PATENT AND TRADEMARK OFFICE
CERTIFICATE OF CORRECTION

PATENT NO. : 5,592,943

DATED : January 14, 1997

INVENTOR(S) : Buhler et al.

It is certified that error appears in the above-identified patent and that said Letters Patent is hereby corrected as shown below:

In column 1, after line 44, insert "Summary of the Invention"

Signed and Sealed this

Fifth Day of January, 1999

*Attest:*

*Attesting Officer*     *Acting Commissioner of Patents and Trademarks*

UNITED STATES PATENT AND TRADEMARK OFFICE
CERTIFICATE OF CORRECTION

PATENT NO. : 5,592,943

DATED : January 14, 1997

INVENTOR(S) : Buhler et al.

It is certified that error appears in the above-identified patent and that said Letters Patent is hereby corrected as shown below:

On the title page; change "Continuation of Ser. No. 43,870, Apr. 7, 1993, Pat. No. 5,396,891." to --Continuation-in-part of Ser. No. 43,870, Apr. 7, 1993, Pat. No. 5,396,891.--

Signed and Sealed this

Fourteenth Day of December, 1999

Q. TODD DICKINSON

*Attest:*

*Attesting Officer*  *Acting Commissioner of Patents and Trademarks*